United States Patent [19]

Traxler et al.

[11] 4,278,665
[45] Jul. 14, 1981

[54] PAPULACANDIN DERIVATIVES AND PHARMACEUTICAL COMPOSITIONS CONTAINING SAME

[75] Inventors: Peter Traxler, Allschwil; Johannes Gruner, Flüh; Jakob Nüesch, Arlesheim, all of Switzerland

[73] Assignee: Ciba-Geigy Corporation, Ardsley, N.Y.

[21] Appl. No.: 844,412

[22] Filed: Oct. 21, 1977

Related U.S. Application Data

[63] Continuation-in-part of Ser. No. 664,336, Mar. 5, 1976, abandoned.

[30] Foreign Application Priority Data

Mar. 13, 1975 [CH]  Switzerland ......................... 3199/75
Oct. 3, 1975 [CH]  Switzerland ....................... 12857/75

[51] Int. Cl.$^3$ ...................... A61K 31/71; C07H 17/04
[52] U.S. Cl. .................................... 424/181; 424/180; 435/74; 536/4; 536/17 R
[58] Field of Search ...................... 536/17, 4, 120, 119; 424/180, 181

[56] References Cited

U.S. PATENT DOCUMENTS

| 3,945,993 | 3/1976 | Schaffner et al. | 536/17 |
| 3,984,393 | 10/1976 | Magerlein | 536/17 |
| 4,029,769 | 6/1977 | Debono | 424/118 |
| 4,031,207 | 6/1977 | Bauer et al. | 424/118 |

OTHER PUBLICATIONS

Ellis, M. B., "Dematious Hyphomycetes", 1971, p. 569.

*Primary Examiner*—Johnnie R. Brown
*Attorney, Agent, or Firm*—Prabodh I. Almaula

[57] ABSTRACT

The new antibiotic "Papulacandin" is obtained by the cultivation of the microorganism *Papularia sphaerosperma* (Pers.) Höhnel, especially of the strain NRRL 8086, under aerobic conditions in an aqueous nutrient medium. There can also be used mutants of said microorganisms. Papulacandin consists of various components A, B, C, D and E, the more important of which are A and B, whose structures have been elucidated to a great extent: they contain only carbon, hydrogen and oxygen. Papulacandin and its components have a strong anti-fungal action, for instance against *Candida albicans*, and can be used for combating infections caused by pathogenic fungi.

17 Claims, 4 Drawing Figures

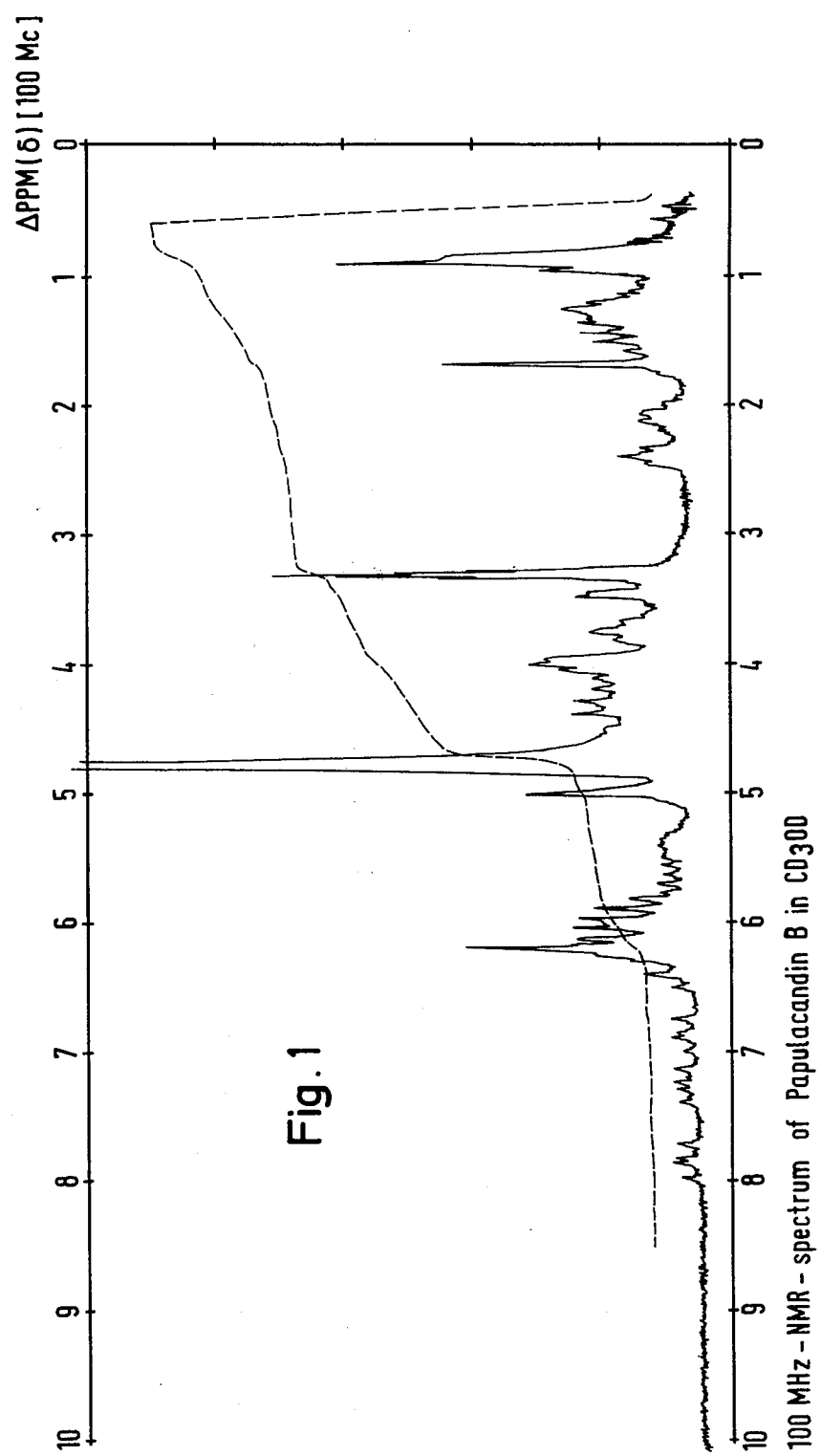

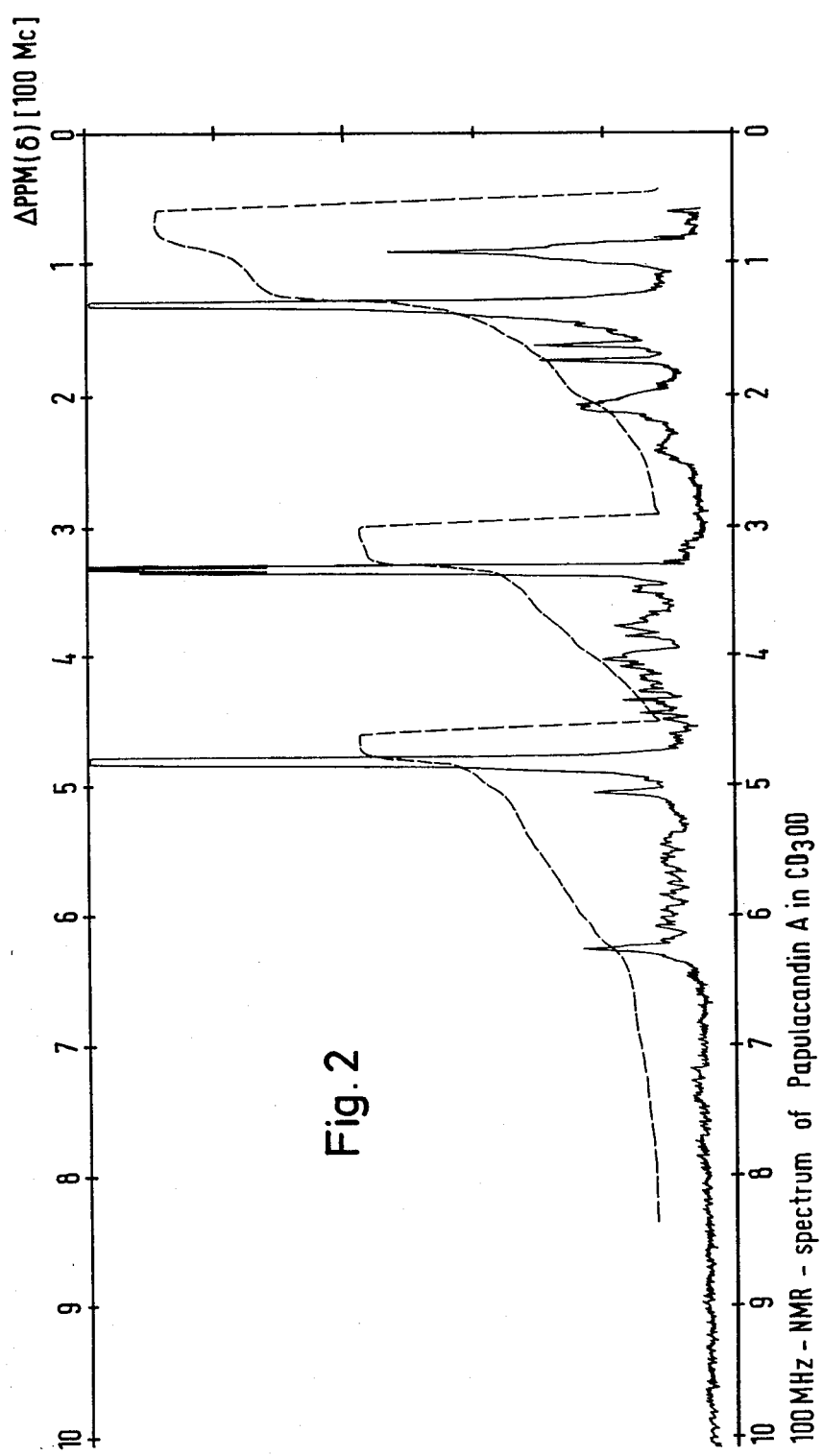

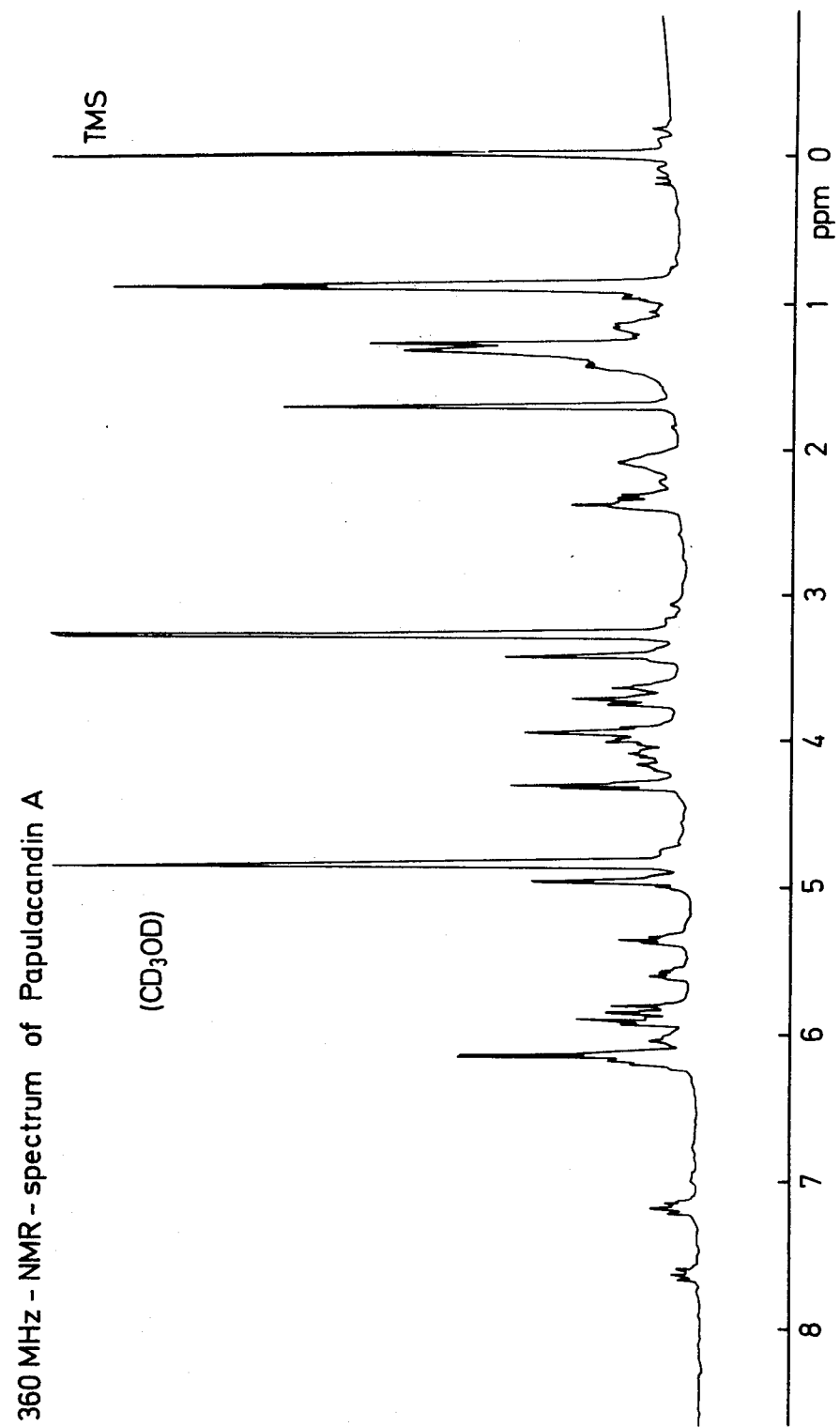

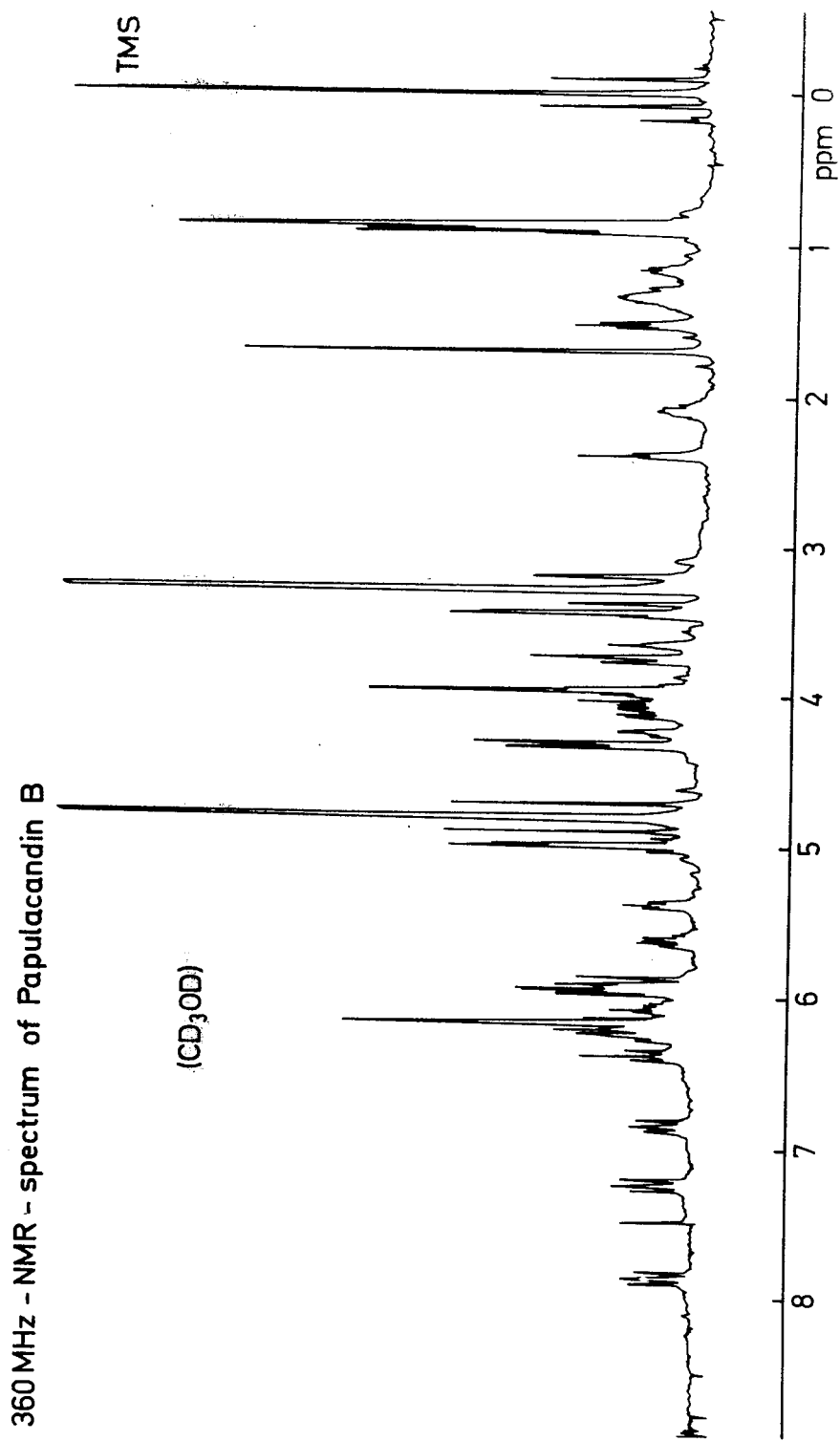

PAPULACANDIN DERIVATIVES AND PHARMACEUTICAL COMPOSITIONS CONTAINING SAME

This is a continuation-in-part of our copending application Ser. No. 664,336, filed Mar. 5, 1976, now abandoned.

The invention relates to the new water-insoluble antibiotic Papulacandin, which is in the form of its principal components A and B as well as a number of secondary components, including components C, D and E, or of mixtures of 2 or more of these components (for the sake of simplicity such mixtures and in particular the mixture as obtained by the fermentation process describes below, are referred to hereinafter as "Papulacandin" [antibiotic A 32283]), and to derivatives of this antibiotic as well as to preparations that contain these compounds, and to a process for obtaining these substances.

The antibiotic Papulacandin is formed when culturing a new microorganism which is kept in our laboratories under the designation A 32283. The strain A 32283 is to be classified among the species *Papularia sphaerosperma* (Pers.) Höhnel, formerly termed *Arthrinium phaeospermum* (Corda) Ellis. The species is described fully by Ellis in Ellis M. B. "Dematious Hyphomycetes" 1971, p. 569 under *Arthrinium phaeospermum*. The strain A 32283 was deposited in the Northern Regional Research Lab., U.S. Department of Agriculture, Peoria, Ill., under No. NRRL 8086.

The antibiotic Papulacandin is formed when culturing the species *Papularia sphaerosperma*, in particular the strain NRRL 8086. Papulacandin is obtained by culturing *Papularia sphaerosperma*, or a mutant that forms Papulacandin, aerobically in an aqueous nutrient solution which contains a source of carbon or nitrogen and inorganic salts until the nutrient solution displays a substantially antibiotic action, and subsequently isolating the antibiotic Papulacandin. The mutants that form the antibiotic Papulacandin can be obtained, for example, under the action of ultraviolet rays or X-rays or from nitrogen-mustard oils. Preferably the strain NRRL 8086 (A 32283) is used.

Examples of carbon sources are: assimilable carbohydrates, for example glucose, saccharose, lactose, mannitol, starch, glycerol, and also inositol. As nitrogen-containing nutrients there may be mentioned: amino acids, peptides and proteins and their degradation products, such as peptone or tryptone, meat extracts, water-soluble constituents of cereal grains, such as maize and wheat, of distillation residues of alcohol production, of yeast, beans, especially of the soya bean plant, of seeds, for example of the cotton plant, and also ammonium salts and nitrates. Of other inorganic salts the nutrient solution can contain, for example, chlorides, carbonates, sulphates, phosphates of alkali metals or alkaline earth metals, of magnesium, iron, zinc and manganese.

The cultivation is carried out aerobically, that is to say, for example, in a quiescent surface culture or preferably immersed while being agitated or stirred with air or oxygen in a shaking flask or a known fermenter. A suitable temperature is one between 18° and 40° C., preferably app. 23° C. As a rule, the nutrient solution exhibits a substantially antibacterial action after 1½ to 5 days. It is preferable to carry out the cultivation in several steps, i.e. to prepare initially one or more precultures in a liquid nutrient medium and then to inoculate the actual production medium with these, for example in the ratio 1:20. The preculture is obtained, for example, by inoculating a liquid medium with a spored mycelium obtained by an approximately 14 day growth on a solid culture medium and allowing it to develop. The antibiotic is isolated from the culture medium by methods which are known per se, taking into account the chemical, physical and biological properties of the antibiotic.

Thus the antibiotic can be extracted from the unfiltered culture broth with an organic solvent which is sparingly soluble in water, for example ethyl acetate. This "whole broth" process is preferably used, because the antibiotic is present both in the mycelium and in the culture filtrate. The antibiotic collects in the organic phase, for example in the ethyl acetate, and this phase is separated from the extracted culture liquid and the "slurry" (extracted mycelium and solid constituents of the nutrient solution). The residue obtained during the extraction can be subjected to one or more repeated extractions with the same solvent or with another solvent.

The mycelium which is filtered off, for example, with filter aids, or the culture filtrate, can also be extracted alone. The mycelium which has been washed with water (together with the filter aid) is preferably extracted with a water-miscible organic solvent, for example a lower alkanol containing 1 to 4 carbon atoms, such as methanol, ethanol, propanol, isopropanol, dimethyl sulphoxide, formamide, dimethyl formamide, methyl acetamide, dioxan, tetrahydrofuran, acetone, or with mixtures of these solvents with water, in particular with aqueous methanol. The culture filtrate is extracted with a water-immiscible solvent, for example ethyl acetate, a water-immiscible alcohol, for example n-butanol, or a higher aliphatic ketone, for example methyl isopropyl.

After the solvent has been evaporated off, the crude product obtained can be purified, for example, by extraction, precipitation, partitioning between immiscible solvent phases, or by adsorption, above all by chromatography. It is thus possible to remove from the crude product, for example the ethyl acetate extract of the culture broth, substantial amounts of impurities by successive simple purification methods, such as extraction of the dried or dissolved crude product with solvents in which the antibiotic is insoluble, for example hydrocarbons such as petroleum ether, cyclohexane, or anhydrous halogenated hydrocarbons, for example methylene chloride, chloroform, carbon tetrachloride. It is also possible to dissolve the crude product, for example in methanol, and to remove impurities from it by adsorption agents, such as activated charcoal, silica gel, magnesium silicate, aluminium oxide, or mixtures thereof, or by adsorption resins, for example crosslinked dextranes such as "Sephadex" ® (Pharmacia Fine Chemicals, Uppsala). The crude product can be purified, for example, by repeated column chromatography using silica gel, advantageously with the addition of small amounts of activated charcoal. The antibiotic is eluted preferably by the gradient method with mixtures of chloroform or carbon tetrachloride and methanol, the percentage content of the stronger polar solvent being increased gradually. When the extract obtained by extraction of the culture broth is chromatographed through a mixture of silica gel with, for example, 5 percent by weight of activated charcoal and, for example, chloroform/methanol as eluant, virtually the entire amount of the antibiotic extracted from the culture broth is found in the eluates of the methanol concentrations 5–20%.

The above distribution between immiscible solvent phases can also be carried out as counter-current distribution in a Craig apparatus. A mixture of ethyl acetate, cyclohexane, methanol and water is used, for example, as solvent system.

The individual unitary components of the antibiotic can be obtained by separating and isolating them by preparative thin-layer chromatography under the conditions described for analytical proof. The separation by means of column chromatography is more advantageous, using for example silica gel which contains 1 to 5% of activated charcoal and effecting elution preferably by the gradient method with a mixture of chloroform and methanol. The increase in the concentration of the more polar solvent is advantageously effected in smaller percentage amounts, for example 5–20% of methanol, or the continuous gradient elution method is used. The antibiotic is preferably eluted at a methanol concentration of 10%. The purification procedure can be repeated, if appropriate.

When carrying out thin-layer chromatography over silica gel (e.g. with chloroform/methanol or ethyl acetate/acetone/water as eluant) and effecting bioautography with Candida albicans, it is possible to isolate at least five active components with antibiotic action whose Rf values in a thin-layer chromatogram on silica gel are reported in Table I. System 1 denotes chloroform/methanol (4:1), two developments, and system 2 denotes ethyl acetate/acetone/water (72:24:4), two developments.

TABLE I

| Substance | System 1 | System 2 |
| --- | --- | --- |
| Papulacandin | | |
| component A | 0.35 | 0.41 |
| component B | 0.27 | 0.32 |
| component C | 0.24 | 0.28 |
| component D | 0.45 | 0.74 |
| component E | 0.47 | 0.51 |

App. 75% of the antibiotic consists of the main component B, app. 10% of component A. In the progressive dilution test with Candida albicans as test organism, minimum inhibitory concentrations (MIC) between 0.006 and 0.1 γ/ml were found for components A and B. Candida albicans is a particularly suitable test organism for testing the antibiotic action in the individual isolating steps as also in the culture medium.

According to elementary analysis of the main components A, B, D and E, and antibiotic consists only of the elements C, H and O.

The antibiotic Papulacandin B possesses the following chemical and physical properties: It is a weakly acid substance, which is white when in powder form. It is soluble in alcohols, for example lower alkanols, such as methanol, ethanol, n-propanol, and in ketones, for example di-lower alkyl ketones, such as acetone, methyl, isobutyl ketone, and also in dimethyl formamide and dimethyl sulphoxide. The compound is sparingly soluble in ethyl acetate and chlorinated hydrocarbons, such as methylene chloride, chloroform and carbon tetrachloride (10–100 mg/l), and is virtually insoluble in water, petroleum ether, hexane. Melting point: 193°–197° C. (with decomposition).

Elementary analysis (calculated for $C_{47}H_{64}O_{17}$): C calc: 62.65%; found: 61.28%, H calc: 7.16%; found: 7.18%.

$[\alpha]_D^{20} = +50.0° \pm 1°$ (c=0.46 in methanol).

UV-spectrum in ethanol: λ max 232 nm ($\epsilon$=42 000); 240 nm ($\epsilon$=42 400); 268 nm ($\epsilon$=44 800); 300 nm ($\epsilon$=31 200).

IR spectrum in KBr, see Example 3.
100 MHz—NMR-spectrum, see FIG. 1.
360 MHz—NMR-spectrum, see FIG. 4.

The molecular weight can be estimated as 900–950 on the basis of the determination of the molecular weight of the acetyl derivative by osmometry in vapour phase. The antibiotic possesses no free carboxyl and no O-methyl groups. Only smaller fragments are detectable in the mass spectrum. A molecule ion is missing. The signals of 45–48 carbon atoms can be observed in the $^{13}$C-NMR spectrum. On the basis of the results of the elementary analysis and of the degradation experiments with Papulacandin, the following empirical formula can be established: $C_{47}H_{64}O_{17}$.

Several hydroxyl groups, among them 2 phenolic groups, could be acetylated with acetic anhydride and pyridine. The number of acetyl groups can be estimated spectroscopically only with difficulty. In the 100 MHz nuclear magnetic resonance spectrum the signals of several acetyl groups are visible at app. 2 ppm. On the basis of the degradation experiments 9 acetyl groups should be present. The molecular weight of 1267 was determined by osmometry. The following physical-chemical data were obtained for the acetyl derivative: elementary analysis (calculated for $C_{65}H_{82}O_{26}$, MW 1278):

C: calc. 61.02%; found: C=60.74%;
H: calc. 6.46%; found: H=6.50%.

UV-spectrum (in ethanol): λ max 216 nm ($\epsilon$=23 200); 242 nm ($\epsilon$=25 600); 268 nm ($\epsilon$=27 600); 295 nm (shoulder).

IR-spectrum, see Example 6.
$[\alpha]_D^{20} = -6° \pm 1°$ (c=0.765 in chloroform).

Upon hydrogenation, Papulacandin B took up 7 moles of hydrogen. All the signals of olefinic protons have disappeared in the $^1$H-NMR spectrum of the hydrogenation product. Two aromatic protons are still visible at 6.3 ppm. The IR spectrum in KBr is indicated in Example 7. The physical-chemical data obtained for the hydrogenation product are as follows:

elementary analysis (calculated for $C_{47}H_{78}O_{17}$): C: calc. 61.69%; found: 60.94%; H: calc. 8.59%; found: 8.56%; O: calc. 29.72%; found: 30.10%; F. 125°–130° C.

UV-spectrum (in ethanol) λmax 270 nm ($\epsilon$=3100); $[\alpha]_D^{20} = +7° \pm 1°$ (c=0.214 in methanol).

The antibiotic Papulacandin component A has the following chemical and physical properties: it is a weakly acid, white substance, when in crystalline form, with the same solubility properties as component B. Melting point: 171°–173° C. (with decomp.).

Elementary analysis (calculated for $C_{47}H_{66}O_{16}$): C found: 61.88% calc. 63.66% found: 62.29%; H found: 7.34% calc. 7.45% found: 7.54%; O: calc. 28.85% found: 29.40% (later results).

UV-spectrum (in ethanol): λ max 232 nm (shoulder); 242 nm ($E_{max}$=425); 265 nm ($E_{max}$=520).

IR-spectrum in KBr, see Example 3
$[\alpha]_D^{20} = +30° \pm 1°$ (c=0.419 in methanol).

FIG. 2 shows the 100 MHz nuclear magnetic resonance (NMR) spectrum and FIG. 3 the 360 MHz-NMR spectrum.

Papulacandin A possesses no free carboxyl and O-methyl groups. Only smaller fragments can be detected in the mass spectrum. A molecule ion is missing.

It was possible to acetylate different hydroxyl groups with acetic anhydride and pyridine. The IR spectrum of the acetyl derivative in methylene chloride is indicated in Example 9. It is difficult to estimate the number of acetyl groups, but there are probably 9 to 11. The acetyl derivative of Papulacandin A has the following physical-chemical properties:

Elementary analysis (calculated for $C_{63}H_{82}O_{24}$, MW 1222): C found: 61.91%, calc.: 61.87%, found: 61.91%; H found: 7.22%, calc.: 6.71%, found: 7.22%; O found: 30.81%, calc.: 31.42%, found: 30.81% (later results).

UV-spectrum (in ethanol): $\lambda$ max 240 nm ($E_{max}=270$); 262 nm ($E_{max}=330$); $[\alpha]_D^{20}=-15°\pm1°$ (c=0.249 in chloroform).

On microhydrogenation of Papulacandin A 6–7 moles of hydrogen are taken up.

The antibiotic Papulacandin component C has the following chemical and physical properties: it is a weakly acidic substance, which it white when in powder form. It is soluble in alcohols, for instance those named above in connexion with Papulacandin component B, and in ketones, dimethylformamide and pyridine. The compound is sparingly soluble or insoluble in the same solvents as named above for Papulacandin B. Melting point: 140°–150° (with decomposition).

Elementary analysis: C found 62.65%; H found 7.16%;

Molecular formula: $C_{47}H_{64}O_{17}$; Molecular weight: 900.

$[\alpha]_D^{22}=+33°\pm1°$ (in methanol).

UV-spectrum in ethanol: $\lambda$ max 232 nm; 240 nm; 268 nm; 297 sh.

Papulacandin C is a stereoisomer of Papulacandin B, as will be shown below.

The antibiotic Papulacandin component D has the following chemical and physical properties. It is a weakly acid, white substance when in powder form, with solubility properties similar to those of component B. m.p. 127°–130° C.

elementary analysis: C found: 62.32%; H found: 7.59%.

UV-spectrum (in ethanol): $\lambda$ max 230 nm ($E_{max}=340$); 235 nm (shoulder);
261 nm ($E_{max}=320$).

$[\alpha]_D^{20}=+7°\pm1°$ (c=0.250 in chloroform).

The IR spectrum in KBr is indicated in Example 5.

The antibiotic Papulacandin component E has the following chemical and physical properties. It is a weakly acid, white substance when in powder form, with solubility properties similar to those of component B.

Elementary analysis: C found: 64.71%; H found: 8.43%.

UV-spectrum (in ethanol): $\lambda$ max 230 nm ($E_{max}=270$); 237 nm (shoulder); 267 nm ($E_{max}=300$), 292 nm (shoulder).

The IR spectrum in methylene chloride is indicated in Example 5.

STRUCTURAL ANALYSIS OF PAPULACANDIN B

Three fragments can be isolated upon alkaline hydrolysis of Papulacandin B in 0.5 normal methanolic potassium hydroxide solution.

Chart 1
Alkaline hydrolysis of Papulacandin B

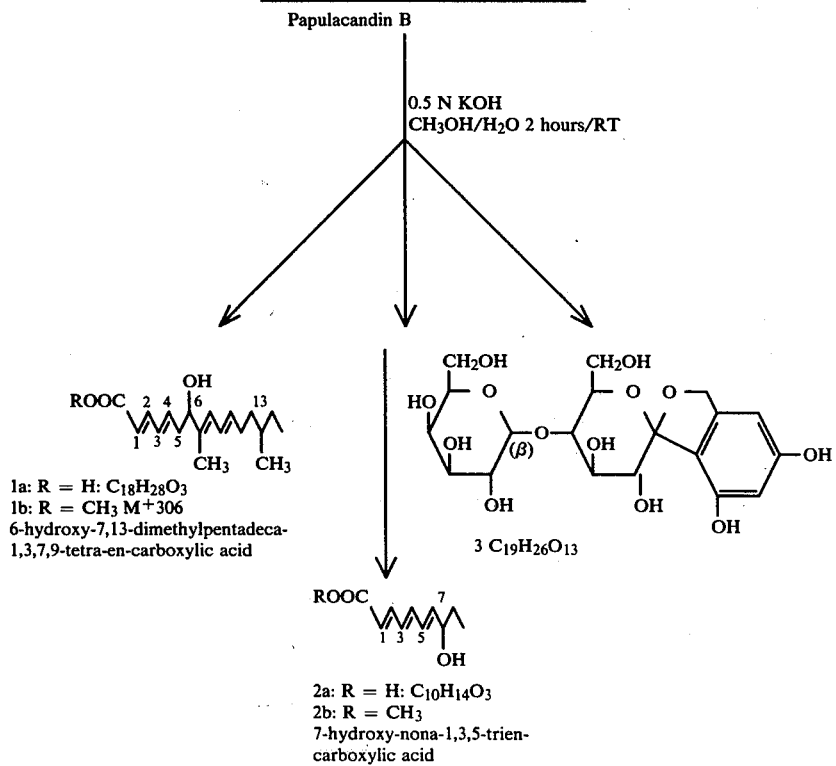

(1) 6-hydroxy-7,13-dimethyl-pentadeca-1,3,7,9-tetra-en-carboxylic acid methyl ester The compound was obtained by extracting the reaction solution with ethyl acetate at pH 7.5 and subsequently esterifying the extract with diazomethane.

The structure of this 4-fold unsaturated fatty acid of 16 carbon atoms was established as follows (see Chart 2):

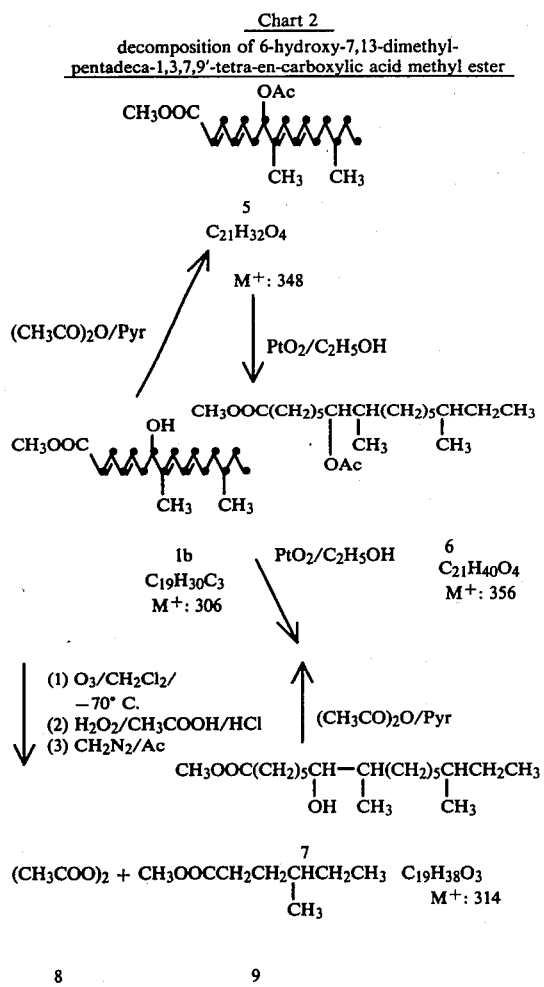

Acetylation of the methyl ester 1b yielded the monoacetate 5 with the mass 348. The 13-position of the methyl group was inferred from the interpretation of the $^{13}$C-NMR spectrum of 5. The hydrogenation product of 5 showed in the mass spectrum a molecule ion at m/e 356. Hydrogenation of the methyl ester 1b on the other hand yielded 7-hydroxy-8,14-dimethylpalmitic acid methyl ester 7 the molecule ion of which was found in the mass spectrum at m/e 314. Its monoacetate was again identical with the above described compound 6. The postulated structure of the aliphatic radical was then established by ozonolysis of the methyl ester 1b. It was possible to detect the presence of oxalic acid dimethyl ester 8 and 4-methylcaproic acid methyl ester 9 in the reaction mixture by gas chromatography separation and comparison with authentic material.

(2) 7-Hydroxy-nona-1,3,5-trien-carboxylic acid methyl ester

The compound was obtained by extracting the reaction solution with ethyl acetate at pH 2.5 and subsequently esterifying the extract with diazomethane. It was possible to establish the above postulated structure with the aid UV, IR and mass spectra (MS, with high resolution) abd nuclear magnetic resonance spectroscopy (with double resonance tests) of the methyl ester.

The structure of this 3-fold unsaturated fatty acid was confirmed by oxidising the methyl ester with $CrO_3$ (Jones reagent) to give the corresponding ketone 4:

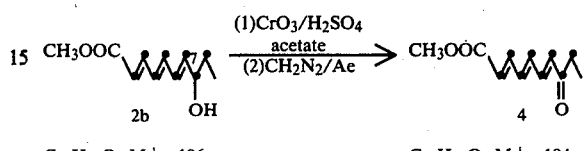

A molecule ion is present at m/e 194 in the MS of the ketone. The proton in 7-position has disappeared in the NMR spectrum.

(3) Sugar fragment $C_{19}H_{26}O_{13}$

This fragment was obtained from the residual reaction solution after neutralisation to pH 7.5 by chromatography through Sephadex-LH-20.

The interpretation of the MS, the 100 MHz and 360 MHz NMR spectra and of the $^{13}$C-NMR spectrum with off-resonance decoupling of the acetate 10a (see Chart 3) confirm the suggested structure.

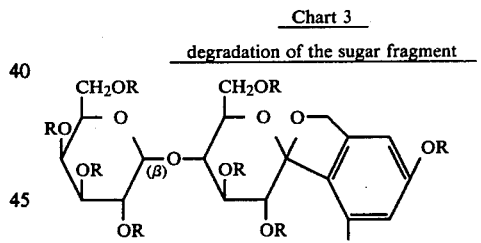

-continued
Chart 3
degradation of the sugar fragment

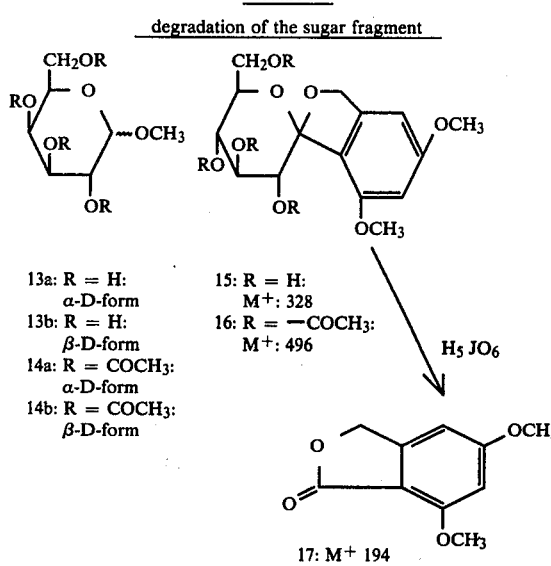

13a: R = H: α-D-form
13b: R = H: β-D-form
14a: R = COCH₃: α-D-form
14b: R = COCH₃: β-D-form

15: R = H: M⁺: 328
16: R = —COCH₃: M⁺: 496

17: M⁺ 194

A molecule ion is found at m/e 840 in the MS of the acetate 10a. Acetylation with deutero-acetic anhydride yielded 10b the molecule ion of which was found in the MS at m/e 867. The presence of 9 acetyl groups is thereby established.

The methanolysis of 3 yielded no satisfactory results. Above all it was not possible to isolate the aromatic fragment. Therefore 3 was converted with diazomethane into the dimethyl derivative 11, which, after acetylation, yielded a hepta-acetate 12 with M⁺ at m/e 784. Methanolysis of 11 then yielded 3 fragments, namely methyl-α-D-galactopyranoside 13a, a small amount of methyl-B-D-galacto-pyranoside 13b whose tetraacetates 14a and 14b were identical to authentic material, and compound 15, which in the MS yielded a molecule ion at m/e 328 (high resolution: $C_{15}H_{20}O_8$). Acetylation of 15 yielded the tetraacetate 16 with M⁺ at m/e 496. Finally the periodate cleavage of 15 using periodic acid yielded compound 17, which in the MS showed a molecule ion at m/e 194. Based on the interpretation of the 360 MHz nuclear magnetic resonance spectrum of 10a, the galactose moiety is attached to the remaining part of the molecule by a β-glycosidic bond.

By adding the empirical formulae of the three fragments, assuming that both fatty acids are attached ester-like to the sugar fragment, the following empirical formula for Papulacandin B: $C_{47}H_{64}O_{17}$, molecular weight 900 results. It is in accord with the results of the elementary analysis.

On the grounds of further analytical examinations, especially of the 360 MHz NMR and ¹³C NMR spectrum and the results of mass spectroscopy the following structural formula for Papulacandin B could be established.

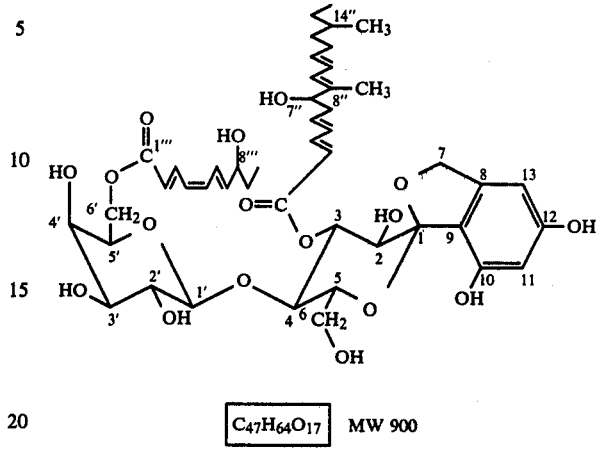

$C_{47}H_{64}O_{17}$   MW 900

STRUCTURE OF PAPULACANDIN A

After spectroscopic comparison of Papulacandin A and Papulacandin B and preliminary hydrolysis experiments, component A also contains 6-hydroxy-7,13-dimethyl-pentadeca-1,3,7,9-tetraen-carboxylic acid and the same sugar fragment and differs in the second fatty acid by one hydroxyl group and one double bond less.

The results of further analytical procedures as those stated above for Papulacandin B have established the following structural formula for Papulacandin A.

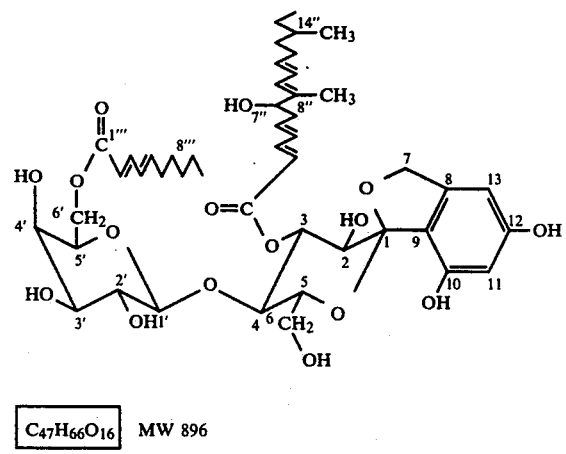

$C_{47}H_{66}O_{16}$   MW 896

On the basis of 360 MHz-NMR-and ¹³C-NMR-spectra and mass spectroscopy the following structural formula for Papulacandin C is made probable.

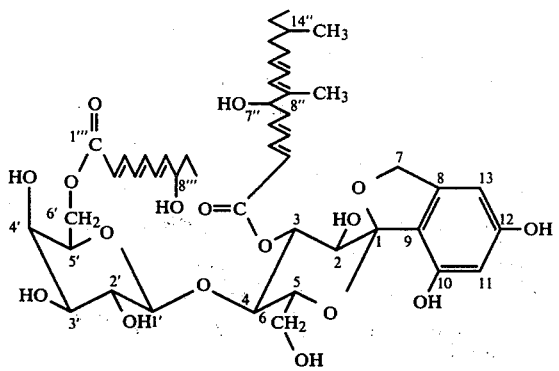

$C_{47}H_{64}O_{17}$ MW 900

Papulacandin component D has the following formula

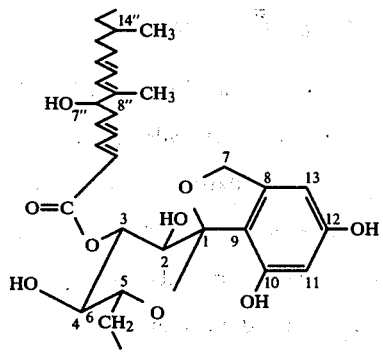

$C_{31}H_{42}O_{10}$ MW 574 as has been established by the analytical methods mentioned above.

The structure of Papulacandin E has not yet been established.

Throughout this specification, derivatives of the antibiotic are to be understood as meaning esters and ethers as well as hydrogenation products and esters and ethers thereof, and especially esters, ethers and hydrogenation products of each of the components A, B, C, D and E and esters and ethers of the hydrogenated components A, B, C, D and E. Esters are, for example, those in which the hydroxyl groups of alcohols are esterified with carboxylic acids or thiocarboxylic acids which contain 1 to 20 carbon atoms. Such acids are above all substituted or unsubstituted lower alkanoic acids containing 1 to 6 carbon atoms, for example formic acid, acetic acid, propionic acid, pivalic acid, substituted or unsubstituted monocyclic or bicyclic aromatic or araliphatic acids, such as benzoic acid, thiobenzoic acid, naphthoic acids, phenyl-lower alkane acids, for example phenylacetic acid, phenyl propionic acids. Substituents of the acids are, for example, halogens, such as fluorine, chlorine, bromine, iodine, trifluoromethyl, nitro, free esterified or etherified hydroxyl groups, for example lower alkanoyloxy, such as acetoxy, lower alkoxy, such as methoxy, lower alkylmercapto, such as methylmercapto, free or functionally modified carboxyl groups, for example lower alkoxycarbonyl, such as methoxycarbonyl, carbamoyl, cyano, substituted or unsubstituted amino groups, for example mono- or di-lower alkylated or N-acylated amino groups, for example methylamino, dimethylamino, lower alkanoylamino, for example acetylamino.

Ethers are in particular compounds in which one or both phenolic hydroxyl groups are etherified with alcohols, primarily with lower alkanols, above all methanol.

The hydrogenation products of Papulacandin either taken as mixture or as single component A, B, C, D or E are especially those resulting from exhaustive catalytic hydrogenation; thus, in the case of Papulacandin A the dodecahydro and in the case of Papulacandin B the tetradecahydro derivatives are to be mentioned, and their esters and ethers as described above.

In addition to their antibacterial action against Hyphomycetes, for example *Trichoderma mentagrophytes*, Papulacandin and its derivatives have above all a very good specific action against various species of yeastlike fungi, such as *Candida albicans*, *Torulopsis dattila*, *Torulopsis famata*, and *Hansenula anomala*. Thus, for example, in the in vitro examination in the gradient plate smear test (W. Szibalski, Science 116, 46[1952], the minimum inhibitory concentration against app. 20 different clinically occurring strains of *Candida albicans* is 0.006 to 0.1 γ/ml. Papulacandin is characterised by very low toxicity in comparison to known antibiotics with antifungal action. The new antibiotic and its derivatives can therefore be used for combating infections which are caused by the fungi referred to hereinbefore, in particular *Candida albicans*, and also as a disinfectant.

The antibiotic Papulacandin and its derivatives can be used, as already mentioned, as a medicine, for example in the form of pharmaceutical preparations. These preparations contain the compounds of the present invention mixed with a pharmaceutical organic or inorganic carrier which is suitable for topical, enteral or parenteral application. Suitable carriers are those substances that do not react with the compound of the present invention, for example gelatin, lactose, starch, magnesium stearate, vegetable oils, benzyl alcohols, or other known medicinal carriers. The pharmaceutical preparations can be in the form of tablets, coated tablets, powders, suppositories, or in liquid form as solutions, suspensions, emulsions, creams or ointments. Where appropriate they are sterilised, and/or contain assistants, such as preservatives, stabilisers, wetting agents or emulsifiers. They can also contain other therapeutically useful substances.

The following Examples illustrate the invention.

The figures represent:

FIG. 1: 100 MHz-NMR spectrum in CD₃OD, Papulacandin B;

FIG. 2: 100 MHz-NMR spectrum of Papulacandin A in CD₃OD;

FIG. 3: 360 MHz-NMR spectrum of Papulacandin A in CD₃OD;

FIG. 4: 360 MHz-NMR spectrum of Papulacandin B in CD₃OD.

EXAMPLE 1

A well-developed culture of *Papularia sphaerosperma* A 32283 on slant agar is suspended in 5 ml of 0.2 m-phosphate buffer at pH 7. Three Erlenmeyer flasks with 1 baffle and each containing 100 ml of nutrient solution which contains 20 g of soya bean flour and 20 g of mannitol per liter of tap water and the pH of which has been adjusted to 8.5 with normal sodium hydroxide solution before the sterilisation, are each inoculated with 5 ml of the Papularia suspension and incubated for 48 hours at 23° C. on a rotating shaking machine with a speed of 250 rpm. 25 ml of the culture obtained in this manner are put into each of 6 two liter Erlenmeyer flasks with 4 baffles and inoculated with 500 ml of the above nutrient solution. The flasks are then incubated at 23° C. on a rotating shaking machine (speed 120 rpm) for 48 hours. Then 1.5 liters of the culture from the 2 liter flasks are transferred to a 50 liter fermenter which contains 30 liters of the above nutrient solution and incubated for 48 hours at 23° C. Then 15 liters of the culture are transferred to a fermenter with 300 liters of the above nutrient solution. This fermenter has a total volume of 500 liters and is equipped with a 6-bladed turbine impeller and 4 baffles. The culturing conditions in the fermenter are: 1 atmosphere (gauge) pressure, stirring speed 450 rpm, temperature 23° C., air flow 1 liter V/V/min. The conditions correspond to an oxygen absorption rate of 200 mmoles of $O_2$/l/hr measured in sulphite solution. The optimum formation of the antibiotic A 32283 takes place after app. 60 hours incubation. The culture solution then has a pH of 6.7. It has an activity of 10–12 mm inhibiting areola in the agar diffusion test with *Candida albicans* using Whatmann A discs with a diameter of 6 mm.

EXAMPLE 2

600 liters of the culture solution obtained in Example 1 are filtered while adding 2% of the filtering air "Decalite" (diatomaceous earth). 560 liters of culture filtrate are adjusted to pH 8.6 and extracted twice with ethyl acetate in the ratio 2:1 in a continuous extractor. The inactive aqueous raffinate is discarded and 600 liters of ethyl acetate phase are concentrated in vacuo to yield a concentrate of 45 liters.

91 kg of mycelium from the above filtration are stirred once with 200 liters of methanol and once with 100 liters of methanol and filtered on each occasion. The inactive mycelium is discarded. Then 300 liters of methanol extract are concentrated in vacuo to yield an aqueous mycelium extract of 33 liters, which is adjusted to pH 8.4 with NaOH and extracted twice with 66 liters of ethyl acetate. The inactive raffinate is discarded.

Then 120 liters of mycelium-ethyl acetate extract are combined with the above 45 liters of culture filtrate-ethyl acetate extract and concentrated in vacuo to yield 1.85 liters of ethyl acetate extract concentrate, which is diluted with 2 liters of 85% methanol and extracted with 3×2 liters of petroleum ether. The inactive petroleum ether phases are discarded and the methanol phase is evaporated to dryness in vacuo to yield 51 g of dark brown viscous residue, which is dissolved in 200 ml of 85% methanol and extracted with 2×300 ml of heptane. The inactive heptane phases are discarded. The methanol phase is concentrated and dried in vacuo.

Yield: 41.8 g of extract residue.

EXAMPLE 3

18 g of the extract residue obtained in Example 2 are chromatographed through a column (diameter: 5.4 cm, height: 140 cm) which consists of a mixture (95:5 weight ratio) of 1000 g of silica gel (Merck, granular size 0.05–0.2 mm) and 50 g of activated charcoal Norit ®. The mixture of silica gel/activated charcoal was suspended beforehand 3 times in methanol and subsequently 3 times with chloroform and filtered. The 12.3 g of extract of residue are dissolved in 50 ml of methanol, mixed with 50 g of silica gel and the mixture is evaporated to dryness. The dried powdery residue is added to the column. The elution is performed in fractions of 1 liter each with chloroform-methanol mixtures while gradually increasing the concentration of methanol, beginning with a methanol content of 4% and ending with 50%. The rate of flow is 500 ml/hr. The fractions are concentrated in vacuo and the residue is dried in a high vacuum. The fractions are then combined on the basis of thin-layer chromatographic and bioautographic examination. Fractions 1–16 (eluted with 1–4% methanol) are only weakly active and are discarded. Fractions 17–23 (eluted with 4 to 7% methanol) contain Papulacandin D and E (further purification see Example 5). Fractions 24–27 (eluted with 7% methanol) contain Papulacandin A. Fraction 28 (eluted with 10% methanol) contains a mixture of Papulacandin A and B. Fractions 29–31 (eluted with 10% methanol) contain Papulacandin B. Fractions 32–36 (eluted with 10–20% methanol) contain Papulacandin C with smaller Rf value in addition to Papulacandin B. The remaining fractions (eluted with 20–50% methanol) contain still further active substances in small amounts.

Papulacandin B is isolated by precipitating it from a solution of the residue of fractions (29–31 (1.86 g) in acetone by the addition of ether. 1.5 g of pure Papulacandin B is thus obtained as a colourless powder with a melting point of 193°–197° C. (with decomp.). Pure Papulacandin A is isolated by crystallising the residue of fractions 24–27 (1.5 g) from acetone/ether to yield 1.2 g of pure Papulacandin A as a colourless powder with a melting point of 171°–173° C.

PAPULACANDIN B

The elementary analysis yields the following values. C=60.45% H=6.99% O=32.6%. In an infrared spectrum in potassium bromide the antibiotic shows bands at 3450, 2975, 2925, 2875, 1690, 1640 (shoulder), 1615, 1465, 1380, 1345, 1300, 1260, 1180, 1150, 1070, 1035, 1005, 970, 865 and 845 cm$^{-1}$.

The UV spectrum in ethanol yields the following maximum values: $\lambda_{max}$232 nm ($\epsilon$=42000), 240 nm ($\epsilon$=42,400), 268 nm ($\epsilon$=44,800), 300 nm ($\epsilon$=31,200). The optical rotation is $[\alpha]_D^{20}=+50+1°$ (c=0.458 in methanol). The empirical formula is $C_{47}H_{64}O_{17}$.

The $^1$H-NMR spectrum in CD$_3$OD is given in FIG. 1. The Rf value is 0.4 in a thin-layer chromatogram over silica gel (silica plates F$_{254}$, Merck) in the system chloroform/methanol (4:1) with triple development. Identification with ultraviolet irradiation, iodine or conc. sulphuric acid and heating. 7 equivalents of hydrogen are taken up in microhydrogenation.

PAPULACANDIN A

The elementary analysis yields the following values: C=62.98% H=7.45% O=29.09%. In the IR spectrum in potassium bromide the antibiotic shows bands at: 3450, 2950, 2870, 1690, 1630, 1610, 1465, 1410, 1380, 1340, 1300, 1265, 1155, 1075, 1035, 1010, 975, 860 and 845$^{-1}$. The UV spectrum in ethanol shows the following maximum values: $\lambda_{max}$(E$_{1\ cm}^{1\%}$): 232 nm (shoulder), 242 nm (E=425) and 265 nm (E=520). The $^1$H-NMR spectrum in CD$_3$OD is reproduced in FIG. 2. The compound has an optical rotation of $[\alpha]_D^{20}=+31°\pm1°$ (c=0.451 in methanol). The Rf value is 0.50 in a thin-layer chromatogram over silica gel (silica gel plates F$_{254}$, Merck) in the system chloroform/methanol (4:1)

after triple development. Identification with ultraviolet irradiation, iodine or conc. sulphuric acid and heating. 6 to 7 equivalents of hydrogen are taken up in microhydrogenation. The approximate empirical formula is: $C_{50-53} H_{72-78} O_{17-19}$.

EXAMPLE 4

2.1 g of the fractions 67-70 containing Papulacandin B and obtained in Example 3 are chromatographed through a column (diameter: 4 cm, height: 50 cm) filled with Sephadex ®-LH-20 (5.5 liters). Sephadex-LH-20 (alkylated crosslinked dextran) was swollen beforehand for 4 hours in methanol. The 2.1 g of Papulacandin B are dissolved in 5 ml of methanol and the solution is passed through the column. Elution is effected with methanol in fractions of 22 ml. The rate of flow is 90 ml/hr. The fractions are freed from solvent in vacuo and the residue is dried in a high vacuum. The eluates of fractions 1-15 (120 mg) are only weakly active and are discarded. Fractions 16-27 contain 1.9 g of pure Papulacandin B, which is precipitated from acetone/ether. For properties, see Example 3.

EXAMPLE 5

The fractions 17-23 (1.5 g) obtained in Example 4 and containing small amounts of Papulacandin D and E are dissolved in acetone. After the solution has stood for some length of time at 0° C. an inactive substance crystallises out. The mother liquor contains enriched Papulacandin D and E. The two components can be separated from each other by preparative thick-layer chromatography over silica gel plates (100 cm×20 cm, thickness of layer 1 mm) in the system ethyl acetate/acetone/water (72:24:4).

Papulacandin D and E are each precipitated as a colourless substance from acetone/ether/hexane.

PAPULACANDIN D the IR spectrum shows, inter alia, bands at 3500, 2950, 2870, 1705, 1675, 1640, 1620, 1465, 1385, 1350, 1300, 1260, 1205, 1150, 1070, 1035, 1005, 975 cm$^{-1}$. For further physical-chemical properties, see the general description.

PAPULACANDIN E the IR spectrum shows, inter alia, the following bands: 3500, 2950, 2870, 1710, 1640 (shoulder), 1615, 1465, 1385, 1350, 1300, 1240, 1185 (shoulder), 1150, 1070, 1040, 1010, 975 cm$^{-1}$. For further physical-chemical properties, see the general description.

EXAMPLE 6

Papulacandin B is acetylated as follows: 250 mg of Papulacandin B are allowed to stand for 3 hours at room temperature with 2 ml of pyridine and 2 ml of acetic anhydride. The reaction mixture is then concentrated in vacuo and chromatographed over 30 g of silica gel with chloroform which contains 1% of methanol to yield 300 mg of colourless, amorphous acetate which is precipitated twice from ether and hexane. The IR spectrum in methylene chloride of the acetyl derivative shows the following bands: 2970, 2870, 1755, 1645, 1620, 1425, 1375, 1225, 1195, 1125, 1080, 1050, 1015, 970 and 890 cm$^{-1}$.

The UV spectrum in ethanol shows maximum values at 216 nm ($\epsilon=23,200$), 242 nm ($\epsilon=25,600$), 268 nm ($\epsilon=27,600$) and 295 nm (shoulder). The elementary analysis gives: C=60.74% H=6.51%. A molecular weight of 1250 was found by osmometry.

EXAMPLE 7

Papulacandin B is hydrogenated as follows: 250 mg of Papulacandin B are added to 50 mg of platinum oxide which have been prehydrogenated in 15 ml of ethanol in a hydrogenating apparatus. The amount of hydrogen taken up is 44 ml corresponding to 6.8 equivalents. After filtration and concentration of the filtrate 243 mg of colourless residue are obtained. This residue is then chromatographed over 50 g of silica gel with chloroform which contains 8% of methanol to yield 106 mg of pure hydrogenation product.

The IR spectrum (in KBr) shows bands at: 3500, 2950, 2860, 1720, 1610. 1465, 1385, 1250, 1185, 1150, 1095, 1070, 1030, 1005, 980 cm$^{-1}$. The signals of the olefinic protons of component B have disappeared in the $^1$H-NMR spectrum. For further physical-chemical properties, see the general description.

EXAMPLE 8

The antibiotic Papulacandin B is methylated as follows: a solution of 200 mg of component B in 2 ml of methanol is allowed to stand at 0° C. for 30 to 45 minutes with a solution of diazomethane in ether. After having evaporated off the solvent 210 mg of residue are obtained. The methyl ether derivative is obtained by preparative thin-layer chromatography over silica gel thick-layer plates in the system chloroform/methanol (5:1). Colourless, amorphous Papulacandin B monomethyl ether (106 mg) is obtained. It is precipitated from acetone/ether/hexane. The IR spectrum (in KBr) shows the following bands: 3450, 2950, 1700, 1640 (shoulder), 1610, 1460, 1440, 1345, 1300, 1260, 1155, 1070, 1030, 1010 cm$^{-1}$. The UV spectrum in ethanol shows the following maximum values: $\lambda_{max}(\epsilon max.)$: 235 (37,600), 267 (39,000), 295 (shoulder).

The $^1$H-NMR spectrum shows the presence of a phenolic methyl group. Papulacandin B dimethyl ether, in which the $^1$H-NMR spectrum shows that both phenolic hydroxyl groups have been methylated, is obtained as further product.

EXAMPLE 9

The ethyl ether of Papulacandin B is prepared as follows: a solution of 1050 mg of Papulacandin B in 30 ml dioxan is allowed to stand at 0° C. for 12 minutes with a solution of diazoethane in ether. After having evaporated off the solvent the residue is chromatographed on a silica gel column (70 g) with chloroform and increasing amounts of methanol (2 to 20%) as eluents. Colorless, amorphous Papulacandin B-monoethyl ether is obtained after precipitation from acetone/ether/hexane. The IR-spectrum (in KBr) shows the following bands: 3500, 2970, 2950, 1710, 1620, 1465, 1380, 1345, 1305, 1265, 1150, 1070, 1035, 1010 cm$^{-1}$. The UV-spectrum (in ethanol) shows the following maximum values: λmax. (εmax.): 235 (40000), 265 (40000), 294 (shoulder). The $^{13}$C-NMR-spectrum shows the presence of an additional ethyl group Papulacandin B-diethylether, in which the $^{13}$C-NMR-spectrum shows that two additional ethyl groups are present, is obtained as further product.

EXAMPLE 10

The propyl ether of Papulacandin B is prepared as follows: a solution of 1 g Papulacandin B in 30 ml dioxan is allowed to stand at 0° C. for 12 minutes with a solution of diazopropane in ether. After having evaporated off the solvent the residue is chromatographed on a silica gel column (70 g) with chloroform and increasing amounts of methanol (2 to 20%) as eluents. Colorless, amorphous Papulacandin B-monopropyl ether is obtained after precipitation from acetone/ether/hexane. The IR-spectrum (in KBr) shows the following bands: 3500, 2970, 2950, 2900, 1705, 1610, 1465, 1380, 1345, 1305, 1265, 1145, 1075, 1035, 1010, 875 cm$^{-1}$. The UV-spectrum (in ethanol) shows the following maximum values: λmax. (εmax.) 233(36800), 267(36000), 294 shoulder. The $^{13}$C-NMR-spectrum shows the presence of an additional propyl group. Papulacandin B-dipropyl ether in which the $^{13}$C-NMR-spectrum shows that two additional propyl groups are present, is obtained as further product.

EXAMPLE 11

The antibiotic Papulacandin A is acetylated as follows: 100 mg of Papulacandin A are left to stand for 3 hours at room temperature with 1 ml of pyridine and 1 ml of acetic anhydride. The reaction mixture is then freed from the solvent in vacuo and the residue is chromatographed over 20 g silica gel with chloroform which contains 1% of methanol, to yield 75 mg of colourless, amorphous acetate, which is precipitated twice from ether and hexane. The IR spectrum (in methylene chloride) of the acetyl derivative shows the presence of the following bands: 2920, 2860, 1755, 1690, 1640, 1605, 1510, 1460, 1370, 1225, 1175, 1125, 1040, 965 cm$^{-1}$. The UV spectrum in ethanol shows maximum values at 242 nm (E$_1$ $_{cm}$$^{1\%}$=240) and 262 (E$_1$ $_{cm}$$^{1\%}$=370). The number of acetyl groups cannot be determined with absolute certainty, but may be presumed to be 9–11 on the basis of the $^1$H-NMR spectrum.

EXAMPLE 12

The antibiotic Papulacandin A is methylated as follows: A solution of 2 g of Papulacandin A in 100 ml of dioxan is allowed to stand at 0° C. for 30 minutes with a solution of diazomethane in ether. After having evaporated off the solvent the residue is chromatographed on a silica gel column (200 g) with chloroform and increasing amounts of methanol (5 to 20%) as eluents. Colorless, amorphous Papulacandin A-monomethyl ether is obtained after precipitation from acetone/ether/hexane. The IR-spectrum (in KBr) shows the following bands: 3500, 2970, 2950, 1710, 1645, 1625, 1465, 1445, 1350, 1270, 1155, 1065, 1035, 1010 cm$^{-1}$. The UV-spectrum (in ethanol) shows the following maximum values: λmax. (εmax.): 237 (34000), 263 (41600). The $^{13}$C-NMR-spectrum shows the presence of an additional methyl group. Papulacandin A-dimethyl ether, in which the $^{13}$C-NMR-spectrum shows that two additional methyl groups are present, is obtained as further product.

We claim:
1. Papulacandin B of the formula

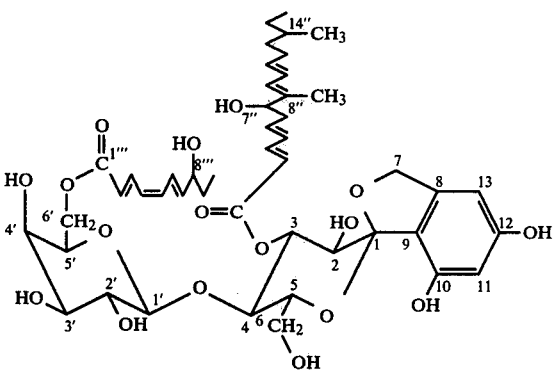

2. Papulacandin A of the formula

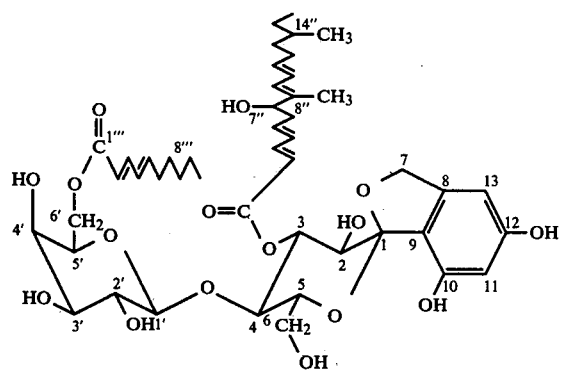

3. Papulacandin C of the formula

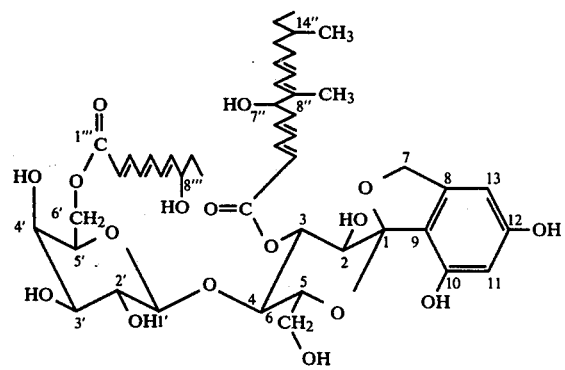

4. Papulacandin D of the formula

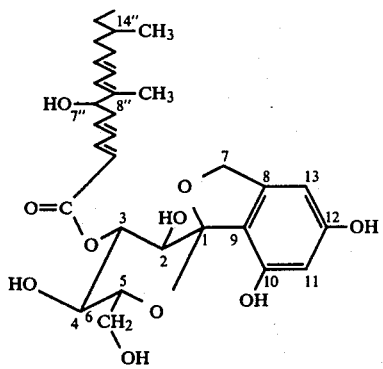

5. A pharmaceutical preparation which comprises an antibiotically effective amount of a compound as claimed in claim 1 together with a pharmaceutical acceptable carrier.

6. A pharmaceutical preparation which comprises an antibiotically effective amount of a compound as claimed in claim 2 together with a pharmaceutical acceptable carrier.

7. A pharmaceutical preparation which comprises an antibiotically effective amount of a compound as claimed in claim 3 together with a pharmaceutical acceptable carrier.

8. A pharmaceutical preparation which comprises an antibiotically effective amount of a compound as claimed in claim 4 together with a pharmaceutical acceptable carrier.

9. A composition of matter comprising Papulacandin A, Papulacandin B, Papulacandin C and Papulacandin D.

10. A derivative of Papulacandin B of claim 1 selected from the group consisting of (a) a mono-phenolic ether, (b) a di-phenolic ether, said ether groups being derived from a lower alkanol, (c) a poly-ester wherein all alcoholic hydroxy groups are esterfied with a lower alkanoic acid, (d) a hydrogenated derivative of said Papulacandin B, and (e) a hydrogenated derivative of said esters and ethers, all non-aromatic double bonds in said hydrogenated derivatives being saturated.

11. A pharmaceutical preparation comprising an antibiotically effective amount of a compound as claimed in claim 10 together with a pharmaceutically acceptable carrier.

12. A derivative of Papulacandin A of claim 2 selected from the group consisting of (a) a mono-phenolic ether, (b) a di-phenolic ether, said ether groups being derived from a lower alkanol, (c) a poly-ester wherein all alcoholic hydroxy groups are esterfied with a lower alkanoic acid, (d) a hydrogenated derivative of said Papulacandin A, and (e) a hydrogenated derivative of said esters and ethers, all non-aromatic double bonds in said hydrogenated derivatives being saturated.

13. A pharmaceutical preparation comprising an antibiotically effective amount of a compound as claimed in claim 12 together with a pharmaceutically acceptable carrier.

14. A derivative of Papulacandin C of claim 3 selected from the group consisting of (a) a mono-phenolic ether, (b) a di-phenolic ether, said ether groups being derived from a lower alkanol, (c) a poly-ester wherein all alcoholic hydroxy groups are esterfied with a lower alkanoic acid, (d) a hydrogenated derivative of said Papulacandin C, and (e) a hydrogenated derivative of said esters and ethers, all non-aromatic double bonds in said hydrogenated derivatives being saturated.

15. A pharmaceutical preparation comprising an antibiotically effective amount of a compound as claimed in claim 14 together with a pharmaceutically acceptable carrier.

16. A derivative of Papulacandin D of claim 4 selected from the group consisting of (a) a mono-phenolic ether, (b) a di-phenolic ether, said ether groups being derived from a lower alkanol, (c) a poly-ester wherein all alcoholic hydroxy groups are esterfied with a lower alkanoic acid, (d) a hydrogenated derivative of said Papulacandin D, and (e) a hydrogenated derivative of said esters and ethers, all non-aromatic double bonds in said hydrogenated derivatives being saturated.

17. A pharmaceutical preparation comprising an antibiotically effective amount of a compound as claimed in claim 16 together with a pharmaceutically acceptable carrier.

* * * * *